(12) United States Patent
Batman et al.

(10) Patent No.: US 8,636,661 B2
(45) Date of Patent: Jan. 28, 2014

(54) EMBEDDABLE MODULES FOR MEASURING BLOOD GLUCOSE LEVELS

(75) Inventors: Carol Batman, Indianapolis, IN (US); Blaine Edward Ramey, Indianapolis, IN (US); Timothy Peter Engelhardt, Avon, IN (US); Michel A. Cadio, Carmel, IN (US); Steven Kent Moore, Carmel, IN (US); Ricky Lee Collins, Cicero, IN (US); Michael L. Brown, Greenwood, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1242 days.

(21) Appl. No.: 12/477,982

(22) Filed: Jun. 4, 2009

(65) Prior Publication Data

US 2010/0312082 A1    Dec. 9, 2010

(51) Int. Cl.
  *A61B 5/00*    (2006.01)
  *G06F 13/12*    (2006.01)

(52) U.S. Cl.
  USPC ............................................. 600/365; 710/63

(58) Field of Classification Search
  USPC ......................................................... 710/63
  See application file for complete search history.

(56) References Cited

U.S. PATENT DOCUMENTS

| | | | |
|---|---|---|---|
| 5,405,511 A | 4/1995 | White et al. | |
| 6,743,635 B2 * | 6/2004 | Neel et al. | 436/95 |
| 6,946,299 B2 * | 9/2005 | Neel et al. | 436/95 |
| 7,041,468 B2 | 5/2006 | Drucker et al. | |
| 2003/0065536 A1 | 4/2003 | Hansen et al. | |
| 2005/0114170 A1 | 5/2005 | Park et al. | |
| 2007/0213605 A1 | 9/2007 | Brown | |
| 2007/0233395 A1 | 10/2007 | Neel et al. | |
| 2008/0119705 A1 | 5/2008 | Patel et al. | |
| 2008/0217407 A1 | 9/2008 | Ackermann et al. | |
| 2008/0319295 A1 | 12/2008 | Bernstein et al. | |

FOREIGN PATENT DOCUMENTS

| | | |
|---|---|---|
| WO | 2006/070196 A1 | 7/2006 |
| WO | 2007081853 A2 | 7/2007 |

OTHER PUBLICATIONS

International Search Report, PCT/EP2010/003360, Oct. 5, 2010, 7 pgs.
International Preliminary Report on Patentability, PCT/EP2010/003360, Sep. 30, 2011.

* cited by examiner

*Primary Examiner* — Frederick Krass
*Assistant Examiner* — Dennis J Parad
(74) *Attorney, Agent, or Firm* — Dinsmore & Shohl, LLP (57) ABSTRACT

An embeddable module for measuring a blood glucose level may be embedded in an external host and may comprise a host interface, a microcontroller, an ASIC, a temperature measuring element, and a measurement strip port. The host interface may permit electrical communication between the host and the microcontroller. The microcontroller and ASIC may communicate with each other and may work together to measure the blood glucose level of a blood sample. The measurement strip port may receive a removable measurement strip having the blood sample. The ASIC may communicate with the measurement strip port such that the ASIC may receive signals from the measurement strip port related to the blood glucose level of the blood sample. The temperature measuring element may be in electrical communication with the microcontroller and may measure the temperature of the module and transmit signals to the microcontroller related to the temperature of the module.

8 Claims, 7 Drawing Sheets

EMBEDDABLE MODULES FOR MEASURING BLOOD GLUCOSE LEVELS

TECHNICAL FIELD

The present invention generally relates to embeddable modules for measuring blood glucose levels and, specifically, to modules which may be embedded in hosts as well as USB devices.

BACKGROUND

As background, persons with diabetes suffer from either Type I or Type II diabetes in which the glucose level in the blood is not properly regulated by the body. As a consequence, many persons with diabetes often carry specialized electronic monitors, called blood glucose (bG) monitors, to periodically measure their glucose level and take appropriate action, such as administering insulin. In addition to the bG monitor, users may also carry a portable electronic device, such as a cellular phone, smart phone, music player, personal digital assistant (PDA), or similar device. In order to reduce the number of electronic devices carried by the person with diabetes, there is a desire for integrating the bG monitor into another portable electronic device. For example, a bG monitor may be integrated into a cellular phone so that a user only has to carry around this single, multi-function device.

In order to facilitate the development of electronic devices having a bG monitor, there is a need for a standardized bG module which may be embedded in various types of portable electronic devices, to which each would then function as a host for the bG module. Such a standardized, embeddable bG module may improve the development cycle by reducing the amount of time necessary for regulatory approval of the host.

Accordingly, a need exists for embeddable modules for measuring blood glucose levels which may be embedded in a host.

SUMMARY

In one embodiment, a blood glucose measurement module embeddable in an external host for measuring a blood glucose level of a blood sample on a disposable measurement strip may comprise a host interface, a microcontroller, an application-specific integrated circuit (ASIC), a temperature measuring element, and a measurement strip port. The host interface is operable to permit electrical communication between the host and the microcontroller such that the module is operable to transmit a result of a blood glucose level measurement to the host. The microcontroller is in electrical communication with the ASIC wherein the microcontroller and the ASIC are operable to measure the blood glucose level of the blood sample. The measurement strip port is operable to receive the disposable measurement strip having the blood sample. The ASIC is in electrical communication with the measurement strip port such that the ASIC is operable to receive signals from the measurement strip port related to the blood glucose level of the blood sample provided on the measurement strip. The temperature measuring element is in electrical communication with the microcontroller and is operable to measure the temperature of the module and transmit signals to the microcontroller related to the temperature of the module.

In another embodiment, a Universal Serial Bus (USB) module for measuring a blood glucose level of a blood sample provided on a disposable measurement strip may comprise a USB interface, a microcontroller, an ASIC, a temperature measuring element, and a measurement strip port. The module is operable to be installed in the USB port of a host. The USB interface is operable to permit electrical communication between the host and the microcontroller such that the module is operable to transmit a result of a blood glucose level measurement to the host. The microcontroller is in electrical communication with the ASIC wherein the microcontroller and the ASIC are operable to measure the blood glucose level of the blood sample. The measurement strip port is operable to receive a removable measurement strip having the blood sample. The ASIC is in electrical communication with the measurement strip port such that the ASIC is operable to receive signals from the measurement strip port related to the blood glucose level of the blood sample. The temperature measuring element is in electrical communication with the microcontroller and is operable to measure the temperature of the module and transmit signals to the microcontroller related to the temperature of the module.

In still another embodiment, a method for a host device to take a blood glucose measurement of a blood sample provided on a disposable measurement strip, wherein the host device comprises an embeddable measurement module comprising a host interface, a microcontroller, an ASIC, a temperature measuring element, and a measurement strip port, comprises inserting the disposable measurement strip into the measurement strip port of the embeddable measurement module; measuring the temperature with the temperature measuring element of the embeddable measurement module; acquiring the blood glucose measurement of the blood sample provided on the disposable measurement strip with the ASIC and microcontroller, the ASIC and microcontroller taking into account the measured temperature; and sending a result of the blood glucose measurement from the embeddable measurement module to the host device via the host interface.

These and additional features provided by the embodiments of the present invention will be more fully understood in view of the following detailed description, in conjunction with the drawings.

BRIEF DESCRIPTION OF THE DRAWINGS

The embodiments set forth in the drawings are illustrative and exemplary in nature and not intended to limit the inventions defined by the claims. The following detailed description of the illustrative embodiments can be understood when read in conjunction with the following drawings, where like structure is indicated with like reference numerals and in which:

DETAILED DESCRIPTION

The embodiments described herein generally relate to embeddable modules which are capable of measuring blood glucose (bG) levels. When installed in an external host having a host processor, the bG module may be used as an embedded measurement engine for a glucose measurement system. The host processor may command the bG module to perform a bG test via the serial interface. Also via the serial interface, the bG module may indicate the status of the bG test as it proceeds, providing feedback to the host such as, what code key is used, when the strip should be inserted, when the blood sample should be applied, and so forth. Once the bG measurement has been successfully completed, the bG module may provide the bG measurement result to the host processor. The host processor may then display and/or store the result. The bG module may be installed in a variety of hosts, such as insulin pumps, music players, cellular phones, smart phones, and personal digital assistants (PDAs).

Figure 1:
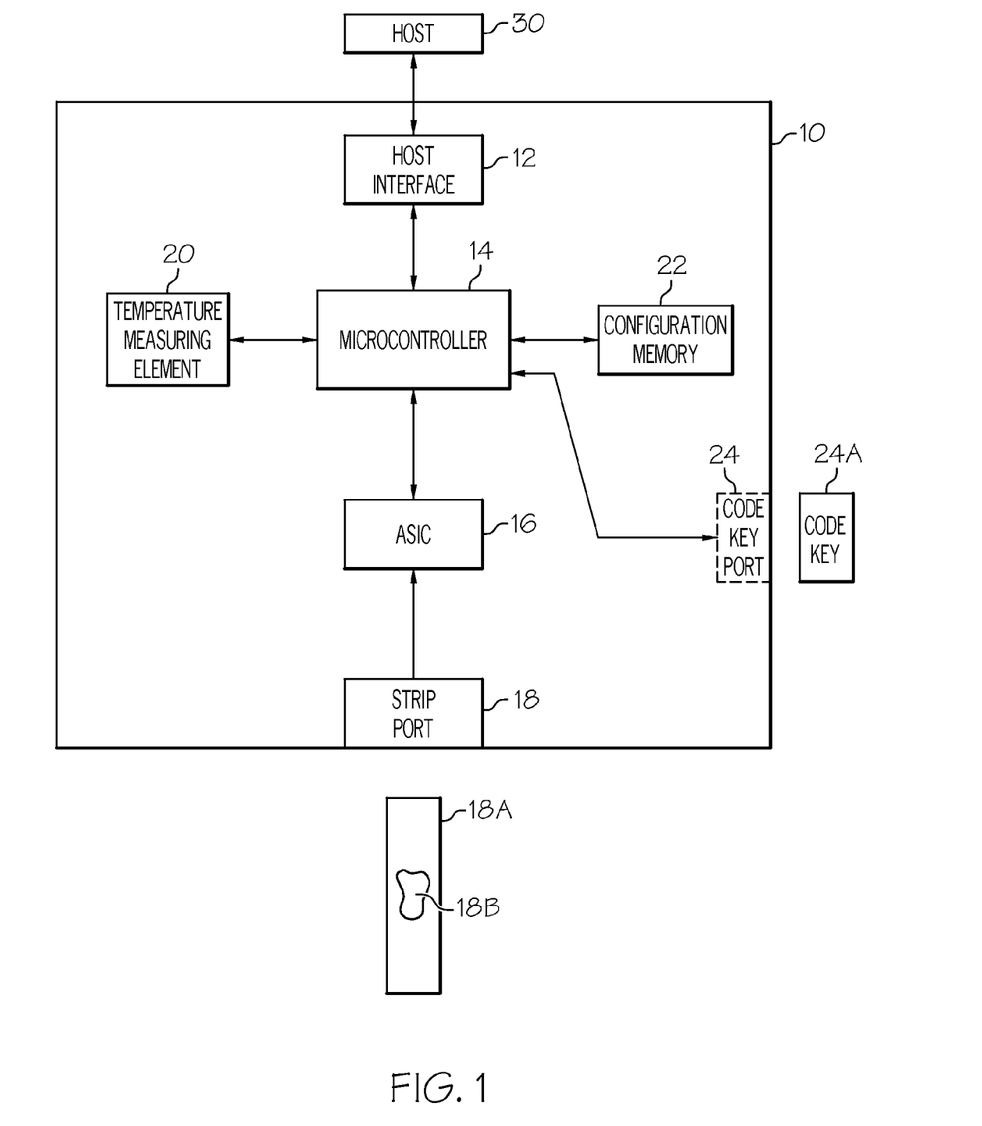
FIG. 1 depicts a schematic of the embeddable module according to one or more embodiments shown and described herein.

In FIG. 1, a schematic representation of an embeddable module 10 for measuring blood glucose levels is shown. The embeddable module 10 may comprise a host interface 12, a microcontroller 14, an ASIC 16, a measurement strip port 18, and temperature measuring element 20. The embeddable module 10 may further comprise a configuration memory 22 and a code key port 24. The embeddable module 10 may be electrically connected to the host 30 through the host interface 12. In addition, a measurement strip 18A may be inserted into the measurement strip port 18 when a bG measurement is performed.

The host interface 12 permits electronic communication between the host 30 and the microcontroller 14. In one embodiment, the host interface may comprise a serial interface, such as a Universal Asynchronous Receiver Transmitter (UART), or other type of serial interface as is known in the art. If the host interface employs a UART, the baud rate may be 9600 or 19,200 bits per second. One byte of serial data may comprise a start bit, eight data bits, a parity bit, and a stop bit. In another embodiment, the host interface 12 may comprise a Universal Serial Bus (USB) connection using a shared differential pair for data transfer. In still another embodiment, the host interface 12 may comprise a parallel interface. The parallel interface may comprise a data bus of a fixed width, such as 4, 8, or 16 bits. In addition, a parallel interface may include control signals to manage the transfer of data between the host and the module. In yet another embodiment, the host interface 12 may comprise one or more discrete signals which have a pre-defined function. For example, the host interface may have a "Module Reset" signal, which may be sent by the host to the embeddable module in order to reset the microcontroller. Other types of discrete signals may be used and may be sent by the host to the module or vice versa.

It is also contemplated that the host interface 12 may comprise any combination of serial, parallel, and/or discrete signals. For example, the host interface may comprise a UART in order to transfer data between the host and the module. This interface may include one or more discrete signals in order to provide other functions, such as "handshaking," resetting, and interrupting. The "handshaking" function may involve asserting signals which indicate that the host or module is ready or is not ready to receive or transmit data. This function may also include signals which indicate whether the host or the module is "sleeping" (i.e., in a low-power sleep mode). The resetting function may permit the host to reset the embeddable module so that the host and module are synchronized. In addition, resetting the module may cause it to perform a self diagnostic and report the results to the host. In this fashion, the host may be able to determine whether the module is functioning properly. The interrupting function may operate to generate a hardware or software interrupt to the microcontroller 14 or to the host processor. As an example, the module may activate an interrupt signal to the host when a measurement strip is inserted into the measurement strip port. The host interface may contain other similar signals which perform functions necessary or convenient for the operation of the module and/or the host.

The host interface 12 may also contain power connections for the embeddable module 10. These power connections may include a power supply signal, often called "Vcc," and a ground. Through these power connections, the host 30 may provide energy to the embeddable module 10 necessary for it to function and make bG measurements. For example, the host may provide a Vcc of 3.3 Volts to the module, which may be consumed by the electronic circuitry on the module, such as the microcontroller, the ASIC, and so forth. Other levels of voltage are also contemplated, such as 5.0 Volts or 2.5 Volts. Furthermore, the host may provide more than one power supply signal for the module. In one embodiment, the host may provide a 3.3-Volt signal for powering the module while it is operating. In addition, the host may provide a second 2.5-Volt connection which could be derived from a battery and can supply power to the module while the host and module are shut off. The return path for the power signal (or signals) may be the ground connection. One or more wires or connector pins may be used to make the power or ground connections.

The host interface 12 may be physically implemented by an electrical connector, thus permitting the interface signals and power signals between the host and the module to be conveniently made. In one embodiment, the connector may provide electrical connectivity (as previously described herein) as well as mechanical connectivity. For example, the host interface 12 may comprise two mating connectors, one on the host and the other on the embeddable module, which, when engaged, mechanically attaches the embeddable module to the host. In this example, the embeddable module 10 may be mechanically coupled to the host 30 by other means as well, such as screws, epoxy, clips, and so forth. In another embodiment, the connector may only provide electrical connectivity. For example, the connector may be a flat-flexible-cable type. Other types and methods of electrically and mechanically connecting the embeddable module to the host are contemplated.

Referring still to FIG. 1, the microcontroller 14 may be in electrical communication with the host interface 12, the ASIC 16, and the temperature measuring element 20. As previously, discussed herein, the microcontroller 14 may be in electrical communication with the host 30 via the host interface 12. In one embodiment, the microcontroller 14 may be model MSP430CG4619, manufactured by Texas Instruments, Inc. Other types and sizes of microcontrollers from Texas Instruments as well as other manufacturers may also be used. In this embodiment, the microcontroller may contain a UART, timers, programmable input/output (I/O) pins, data memory, program memory, and other functions which may facilitate its operation in the embeddable module. The microcontroller may execute a computer program, hereinafter called "module software," which defines and/or enables the functioning of the embeddable module. The module software may be written in a computer language, such as "C" or assembly language, and may be stored in the microcontroller's program memory. The module software may be loaded into the microcontroller either before or after it is placed on the module. The operation of the module software will be discussed herein below.

The microcontroller 14 may require an oscillator or crystal of relatively constant frequency in order function properly. In one embodiment, the oscillator function may be part of the microcontroller itself. In another embodiment, the oscillator or crystal may be external to the microcontroller. For example, the ASIC 16 may be capable of generating an oscillator signal which it may send to the microcontroller. In this case, the frequency of the oscillator signal may be 32,768 Hertz (Hz). It is contemplated that other methods of generating this signal and other frequencies may also be used.

In FIG. 1, the ASIC 16 may be in electrical communication with the microcontroller 14 as well as the measurement strip port 18. The ASIC (also known as an "application-specific integrated circuit") may be a mixed-signal device, having both digital and analog components. When a measurement strip 18A is inserted into the measurement strip port 18, the ASIC may be operable to electrically detect the insertion and, subsequently, communicate with the measurement strip 18A such that the ASIC may receive signals from the strip related to the blood glucose level of a blood sample 18B placed on the strip. The ASIC may, after receiving the signals from the strip, process these signals and communicate information about the bG level to the microcontroller. The microcontroller, in turn, may take this information and process it further in order to arrive at the final bG measurement result. Thus, the ASIC and the microcontroller may work together to perform the bG measurement function, with the ASIC performing part of the function and the microcontroller performing part of the function. The ASIC may be housed in an electrical ball-grid array (BGA) package or other suitable package. The ASIC may additionally perform other functions which may be convenient for the operation of the module. For example, the ASIC may generate a fixed-frequency clock signal for the microcontroller. The ASIC and microcontroller may communicate with each other via a serial bus, such as I²C or SPI, or via a parallel interface.

FIG. 1 schematically depicts the measurement strip port 18 which may be in electrical communication with the ASIC 16. The strip port 18 may be operable to receive a measurement strip 18A, which may be removably inserted in the strip port 18. The measurement strip may contain electronic circuitry and/or chemicals which facilitate the measurement of the bG level of a blood sample 18B. Accordingly, the strip port 18 may have a plurality of electrical pins which matingly engage corresponding pins on the measurement strip 18A when it is installed in the strip port. In one embodiment, the strip port and strip may have six connections or pins. In another embodiment, the strip port and strip may have eight connections or pins. The strips may only be used one time for a measurement since the chemicals on the strip may be consumed during a measurement and the strip may become soiled with the blood sample. Thus, a plurality of strips is typically carried by the user since a number of bG measurements are often taken throughout the day.

In the embodiment shown, the measurement strip port 18 may be located on the embeddable module 10. This location may improve the accuracy of the measurement for two reasons. First, the temperature of the measurement strip may affect accuracy of the measurement due to, for example, the chemicals used on the strip or a characteristic of the blood sample. Second, estimating the temperature of the strip (by the embeddable module) may be more accurately performed when the measurement strip port 18 is physically located on the embeddable module 10. As a result, the temperature measuring element 20 (described herein below) may be used to estimate the temperature of the measurement strip. Because the measurement strip (and blood sample) may reside on the outside of the host, and the temperature measuring element 20 may reside on the inside of the host, any heat generated by the embeddable module or the host circuitry may affect the temperature measurement. The chemical reaction used to measure the glucose level is typically specified for accuracy over a restricted temperature range, so a temperature indication that is higher than the temperature at the reaction site may cause the meter to improperly disallow a test, or perhaps more seriously, may allow a test to be performed below the minimum specified temperature range. Consequently, specific techniques and/or algorithms may be used to estimate the temperature of the measurement strip, one of which may be described in the co-pending and co-owned U.S. Pat. No. 8,140,294, filed Jun. 5, 2009, and entitled Temperature Estimations in a Blood Glucose Measuring Device.

Referring again to FIG. 1, the temperature measuring element 20 may be used to measure the temperature of the embeddable module 10 and to estimate the temperature of the measurement strip 18A. The temperature measuring element may be in electrical communication with the microcontroller such that the microcontroller may request a temperature measurement during a bG measurement or any other time. In one embodiment, the temperature measuring element may comprise a thermistor, the resistance of which is a known function of temperature. Other embodiments may use similar devices, such as semiconductor temperature sensors, resistance thermal devices (RTDs) and thermocouples. As discussed above, the temperature measurement may be used to improve the accuracy of the bG measurement. In addition, the temperature measurement may also indicate conditions in which the bG measurement should not be made, such as when the ambient temperature of the host is outside the operating range of the measurement strip. For example, a measurement strip may be designed to operate from 10 degrees C. to 40 degrees C. Outside this range, the measurement strip may not produce sufficiently accurate results. Thus, when the ambient temperature falls outside this range, the embeddable module (via the temperature measuring element) may recognize this condition and inform the host accordingly. In addition, the module may refuse to take a measurement under such conditions, since the result may not be sufficiently accurate.

Referring still to FIG. 1, the embeddable module 10 may also include a non-volatile configuration memory 22. This memory may be external to the microcontroller 14, as is depicted in FIG. 1, or may be integrated into the microcontroller 14. The memory 22 may be operable to store information relating to the operation of the module, such as configuration parameters, calibration data for the measurement strips, and so forth. The memory 22 may in electrical communication with the microcontroller 14 such that the data stored in the memory may be read by the microcontroller. In addition, the microcontroller may write data to the memory such that the data is stored on the memory in a non-volatile fashion. The fact that the memory 22 is non-volatile may mean that the memory retains the data stored on it, even in the absence of power. The memory, when it is external to the microcontroller, may be a 64 kilobit device, such as a 25AA640A device from Microchip Technology, Inc. Other types of memory, including flash memory, may be used as well.

In FIG. 1, the embeddable module 10 may also include a code key port 24. This port may allow the user to install an external code key 24A which may contain calibration information related to the measurement strip 18A. This calibration information may permit the embeddable module to maintain the accuracy of the bG measurement due to, for example, slight variations in the measurement strip which may have been introduced during the manufacturing process. Thus, in order to maintain the accuracy of the bG measurement, the measurement strip (or, typically, package of strips) may also include a code key 24A which is operable to store information relating to calibration data for the strip (or package of strips). When inserted into the code key port 24, the calibration information contained on the code key 24A may be read by the microcontroller 14. As a result, when a bG measurement is performed, the code key may provide calibration information which permits the microcontroller to maintain the accuracy of the bG measurement.

Figure 2:
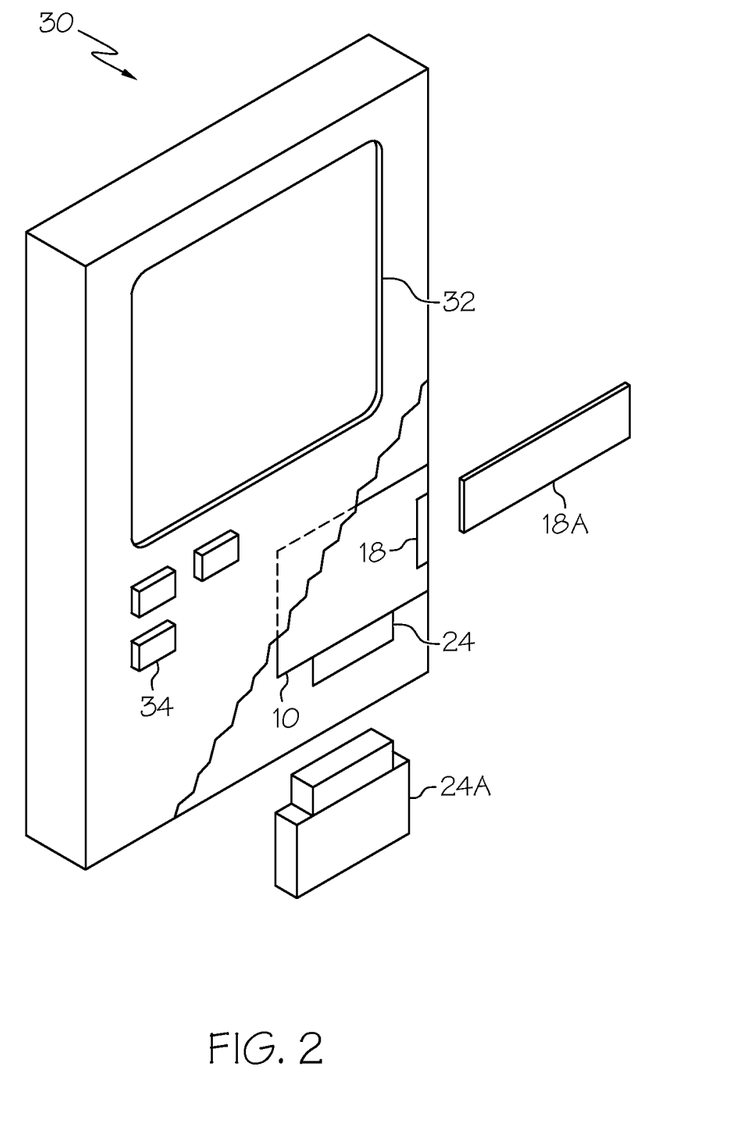
FIG. 2 depicts an embeddable module and a host according to one or more embodiments shown and described herein.

Referring now to FIG. 2, in one embodiment the code key 24A may comprise a device external to the host 30 as well as the embeddable module 10. The code key 24A may be removably inserted into the module 10 by the user. The code key 24A may provide calibration data for a measurement strip 18A or a series or package of strips. The embeddable module 10 may function such that the code key 24A must be inserted for a bG measurement to proceed. In an alternative embodiment, the code key 24A may not have to be installed for a bG measurement to proceed. The code key may possess a mechanical handle such that, when installed into the code key port, the user can insert a fingernail beneath the handle in order to easily remove it.

Although FIGS. 1 and 2 show the code key 24A as being removably installed in the embeddable module 10, in other embodiments the code key port 24 may be physically implemented outside the embeddable module 10, such as in another part of the host 30. In this embodiment, the code key port may be placed on another circuit board in the host. For this embodiment, the host 30 (e.g., host processor) may be in direct electrical communication with the code key port 24 such that the host may read the calibration data contained on the code key 24A when the code key is installed in the code key port 24. When read by the host, the calibration data may be communicated to the microcontroller 14 via the host interface 12. In this fashion, the embeddable module 10 may still receive calibration data for the measurement strip even though the code key is not in direction communication with the embeddable module.

In yet another embodiment, the code key port (and corresponding code key) may be omitted from the module 10 as well as the host 30. In this embodiment, the calibration data may be procured by the host 30 using a wired or wireless communication scheme. For example, the measurement strip may contain identifying information such that, when inserted into the measurement strip port 18, the ASIC 16 is operable to read the identifying information and electronically pass it to the microcontroller 14. The microcontroller may, in turn, request that the host 30 (via the host interface 12) procure the calibration data for that particular measurement strip (having that particular identifying information). The host may wirelessly request the calibration data through a wireless network, such as a 3G cellular network or similar network. The calibration data may be electronically available from a database established by the manufacturer of the measurement strip. After the host wirelessly procures the calibration data, it may finally pass the calibration data to the microcontroller (via the host interface) to be used for the bG measurement. The calibration data procured in this fashion may be stored in the non-volatile calibration memory 22. It should be known that other methods and techniques for procuring the calibration data are contemplated.

Referring again to FIG. 1, the embeddable module 10 is operable to be configured for a specific host 30, both from a hardware and a software perspective. From the hardware perspective, the module 10 may or may not include a code key port 24, as previously discussed herein. When included, the code key port 24 may reside on the module 10 or the host 30. When not included, the code key port 24 may be omitted from both the module and the host, and the calibration data stored on the code key may be procured by another method, such as through a wireless means.

Another configurable hardware feature may be the host interface 12. The host 30 may operate on a different power supply than the module. For example, the host may operate at 5 Volts, and the module may operate at 3.3 Volts. Alternatively, the host may be operable to remove the supply voltage from the module in order to save battery power when the module is not being used. In this situation, a "level translation" device may permit the signals from the host to be properly transmitted to the module, and vice versa.

When host interface employs a serial communication scheme, the serial data interface may employ a "hard-wired" scheme, such a UART. In this embodiment, the communication signals between the host and the module may be implemented with electrical conductors. Furthermore, the connection may be made through an electrical connector. The UART may employ two signals: One signal may transmit data from the host to the module, and the other signal may transmit data from the module to the host. In another embodiment, the host interface may use an infrared data communication scheme, such as one defined by the Infrared Data Association (IrDA). In this case, the host and the module both may have the appropriate circuitry to implement the IrDA protocol, including but not limited to light emitting diodes (LEDs) and photo-sensitive transistor. The data may be transmitted from the host to the module, or vice versa, in the following fashion. The sender may transmit a series of infrared pulses by manipulating a photo diode. The receiver may receive these infrared pulses via a photo-sensitive transistor, which may translate the pulses into electrical signals for the embeddable module or external host. When the host interface uses IrDA protocol, the only "hard-wired" connection between the module and the host may be the power supply, as previously discussed herein.

From the software perspective, the module software executing on the microcontroller 14 may be configured to operate in a number of different ways. As an example, the host interface software may be configured through software registers so as to implement specific message types. Additionally, the module software may be configured to receive the measurement strip calibration data from either a code key port (resident on the module) or from the host. Furthermore, timing parameters may be configured, such as the length of a timeout for a failed message. It is contemplated that other software features may be configured as well.

The configuration of the module (either hardware or software configuration) may be performed via hardware jumpers and/or software registers. The module may provide hardware jumpers, which permit a user to configure the module by removing and/or installing the jumpers. For example, a jumper may be installed in one location in order to set up the host interface to use a hard-wired UART, while another jumper may be installed in a different location in order to set it up for IrDA. Software registers may also be used for a similar purpose. The software registers may be located in the non-volatile configuration memory 22. The hardware jumpers may be set by a user, since this involves physical removal and installation of jumpers. The software configuration registers may be established or changed when the module is manufactured, tested, and/or installed in the host. Furthermore, the software configuration registers may be established or changed through the host after the module is installed. It is contemplated that hardware jumpers may be used to configure hardware features and/or software features. Likewise, it is contemplated that software registers may be used to configure hardware features and/or software features.

In FIG. 2, one embodiment of the embeddable module 10 and a host 30 are depicted. The module 10 may be embedded in the host 30. The host may have a monitor 32, keys 34, and/or a touch screen (not shown). This embodiment depicts the module near the lower right side of the host. However, it is contemplated that the module may be disposed in other locations within the host. For example, the module may be disposed near the upper left side of the host. Alternatively, the module may be disposed in the center of the host.

The measurement strip port 18 may be disposed in any number of locations in the host 30 such that user may be permitted to insert a measurement strip 18A into the strip port 18. For example, FIG. 2 depicts the measurement strip port 18 as being disposed near the right outside edge of the host 30. The measurement strip 18A, in this embodiment, may be inserted from the right side of the host 30 (and into the measurement strip port 18) by the user. In other embodiments, the measurement strip 18A may be inserted from the left, top, bottom, front, or rear of the host. The design of the module 10 and the disposition of the module within the host 30 may define the location of the strip port 18 and from which direction the user may insert the measurement strip 18A.

Figure 3A:
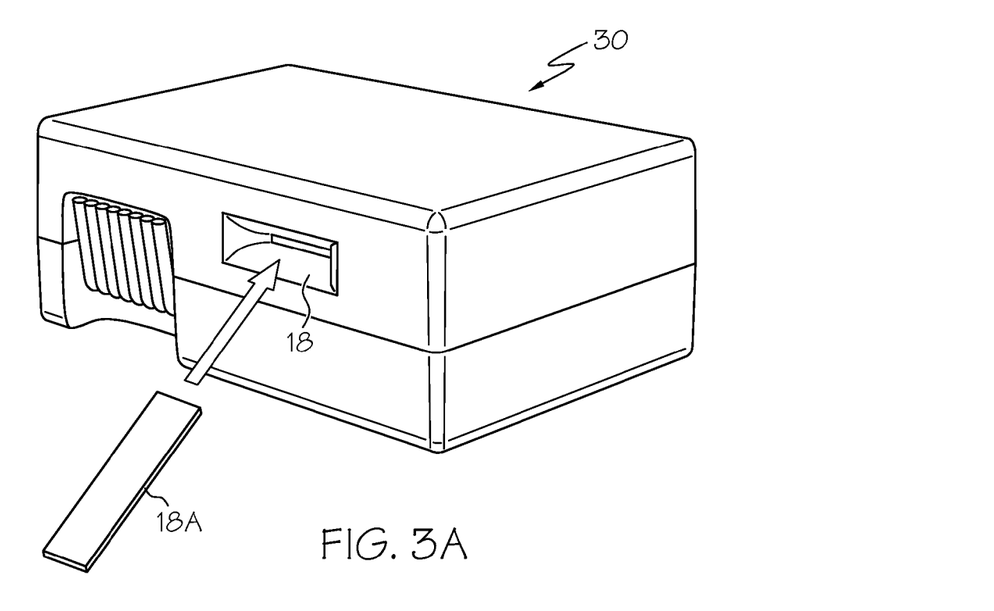
FIGS. 3A and 3B depict a measurement strip port according to one or more embodiments shown and described herein.
Figure 3B:
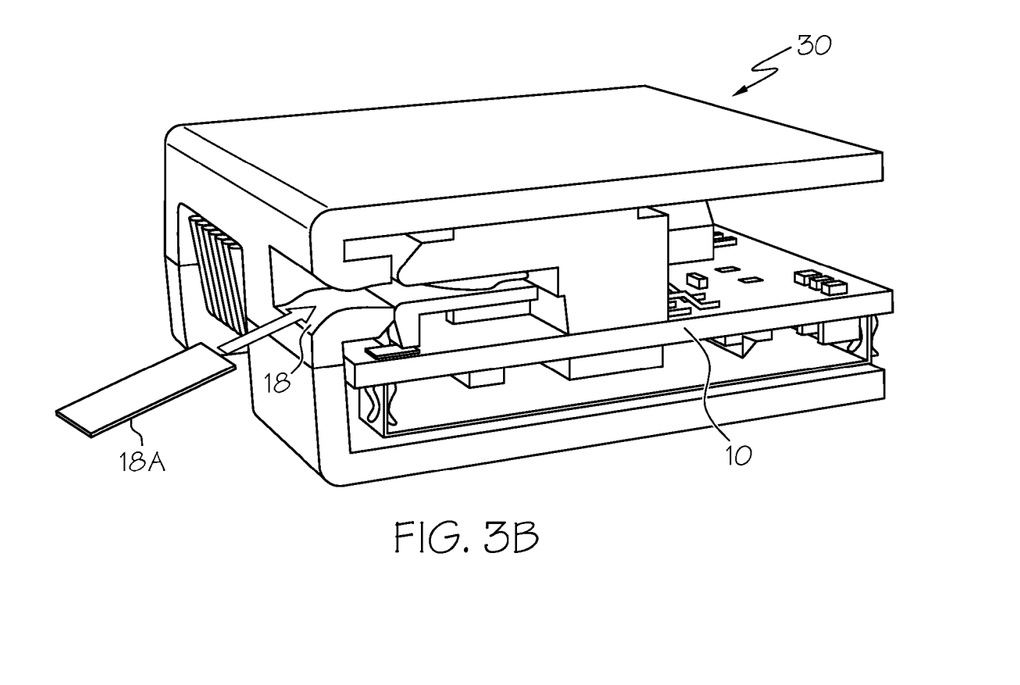

FIGS. 3A and 3B show the details of the measurement strip port 18 according to one embodiment. In FIG. 3A, a slot for the measurement strip 18A may be integrated into the housing of the host 30. The geometry of the slot may provide enough chamfer and guiding surfaces to ease the insertion of the strip into the port. FIG. 3B depicts a cutaway view of the host, showing the slot as well as the measurement strip port 18. When the strip is inserted into the slot, the contacts on the strip make electrical contact with those on the strip port. Other embodiments of the slot and the strip port are also contemplated.

The code key port 24, if used, may likewise be disposed in any number of locations in the host 30. As shown in the embodiment in FIG. 2, the code key port may be located at the bottom of the host. If the code key port 24 is physically placed on the embeddable module 10 (as is shown), then the design of the module and the disposition of the module within the host 30 may define the location of the code key port 24 and from which direction the user may insert the code key 24A. If the code key port is not physically placed on the embeddable module, but is placed in the host, the design of the host 30 then defines the location of the code key port 24. Embodiments which do not employ a code key port 24 may, of course, completely dispense with the port (either in the host or on the module).

Figure 4A:
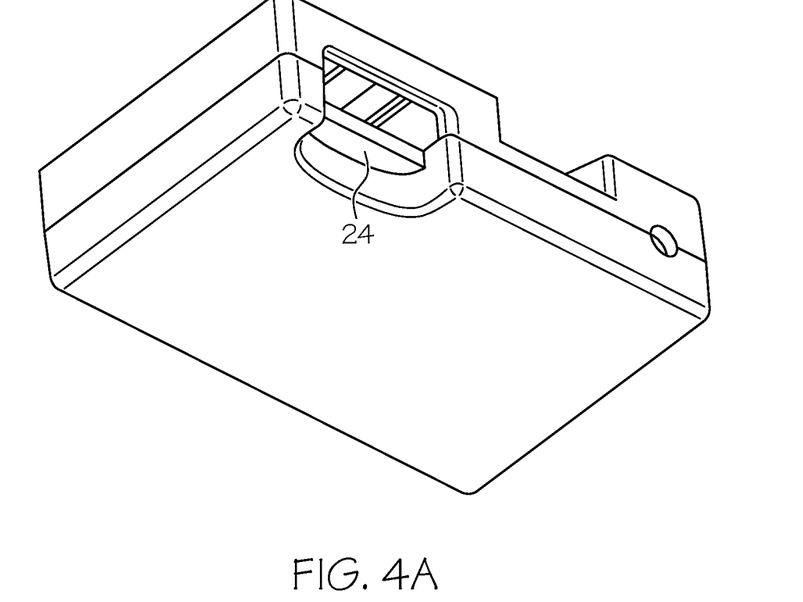
FIGS. 4A and 4B depict a code key port and code key, respectively, according to one or more embodiments shown and described herein.
Figure 4B:
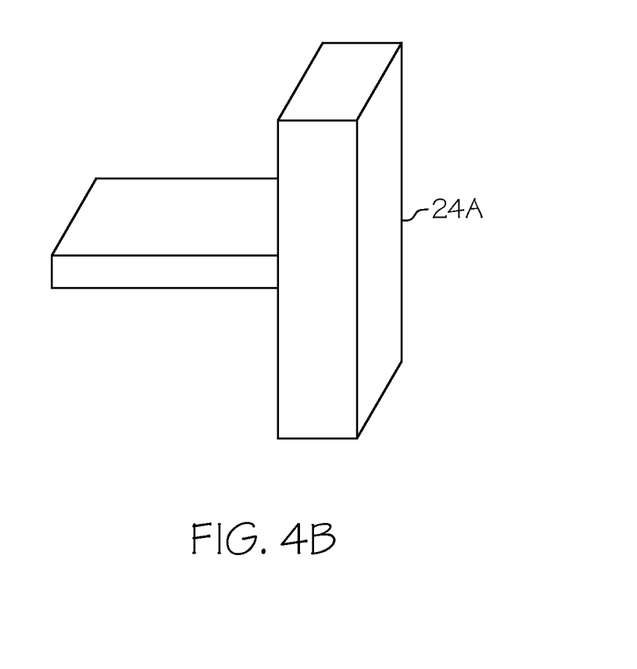

In FIGS. 4A and 4B, exemplary details of the code key port and the code key are shown. The code key port 24, if used, may require a code key 24A to be inserted in order for the calibration data to be read by the module or by the host. FIG. 4A shows one embodiment of the code key port 24 in a host 30. The code key port may be slotted such that a code key may be slidingly inserted into it. The code key 24A may assume a variety of designs, one of which is depicted in FIG. 4B. The code key may comprise a plastic housing in which a circuit board is installed. The edge of the circuit board may extend beyond the edge of the plastic housing so that, when installed in the code key port, the circuit board makes electrical connection with the electrical contacts of the code key port. Other embodiments of the code key are contemplated, including USB modules, Memory Sticks, and so forth.

Figure 5:
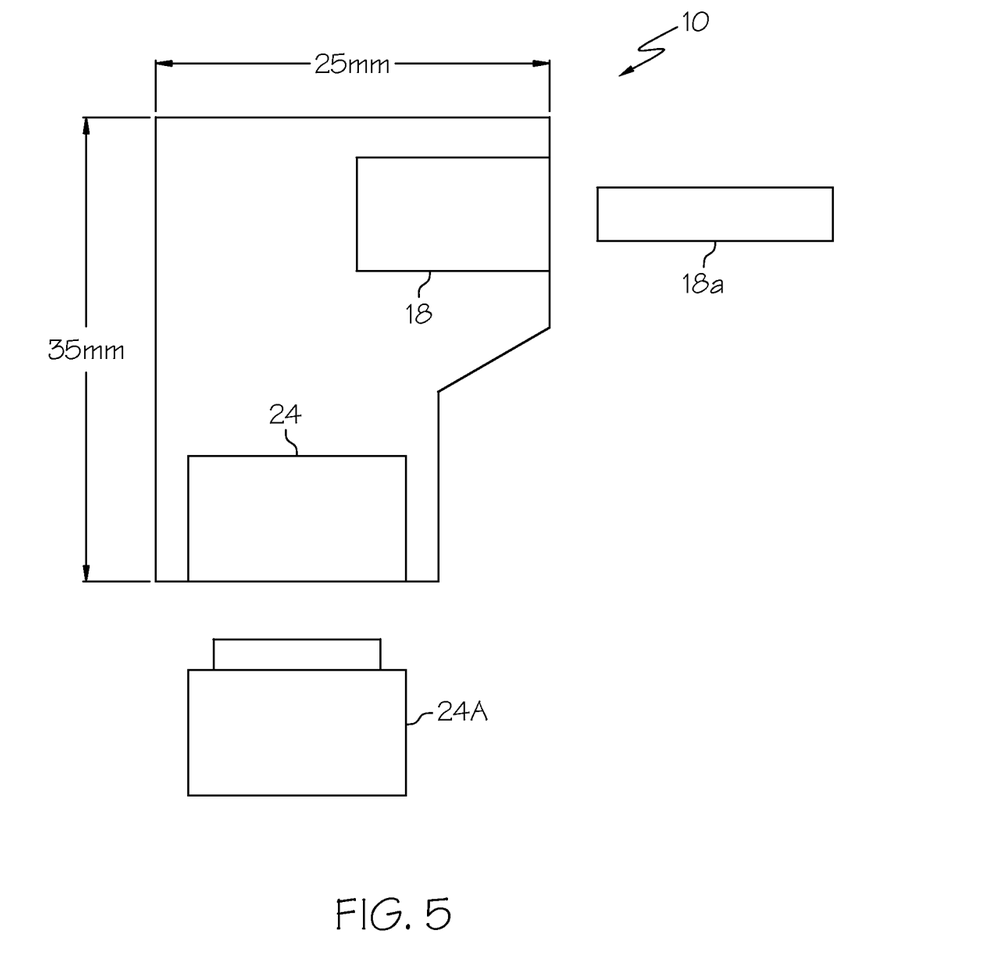
FIG. 5 depicts an embeddable module according to one or more embodiments shown and described herein.

Referring to FIG. 5, one embodiment of the embeddable module 10 is depicted. In this embodiment, the module may comprise a rigid circuit board approximately 35 millimeters (mm) in length and 25 mm in width. The circuit board may be 1.5 mm thick. The components comprising the embeddable module 10, such as the microcontroller and the measurement strip port 18, may be soldered to the circuit board and may be placed on either side of the circuit board. Other shapes and/or thicknesses of the embeddable module are contemplated. Another embodiment of the module may comprise a flat flexible circuit to which the components are soldered. The flat flexible circuit may be operable to bend as it is installed in the host.

Although the primary components of the embeddable module 10 have been described (e.g., the microcontroller, the ASIC, etc.), the module may comprise additional components, such as but not limited to resistors, capacitors, inductors, transformers, transistors, and diodes. These additional components may be used to facilitate the operation of the module. For example, one or more capacitors may be electrically connected to the power supply voltage in order to provide filtering for the module. As another example, inductors may be placed between the microcontroller and the measurement strip port so as to reduce the possibility of damage to the microcontroller due to an electrostatic discharge from the user when inserting the measurement strip. Additional electronic components may be used to perform similar functions.

Figure 6:
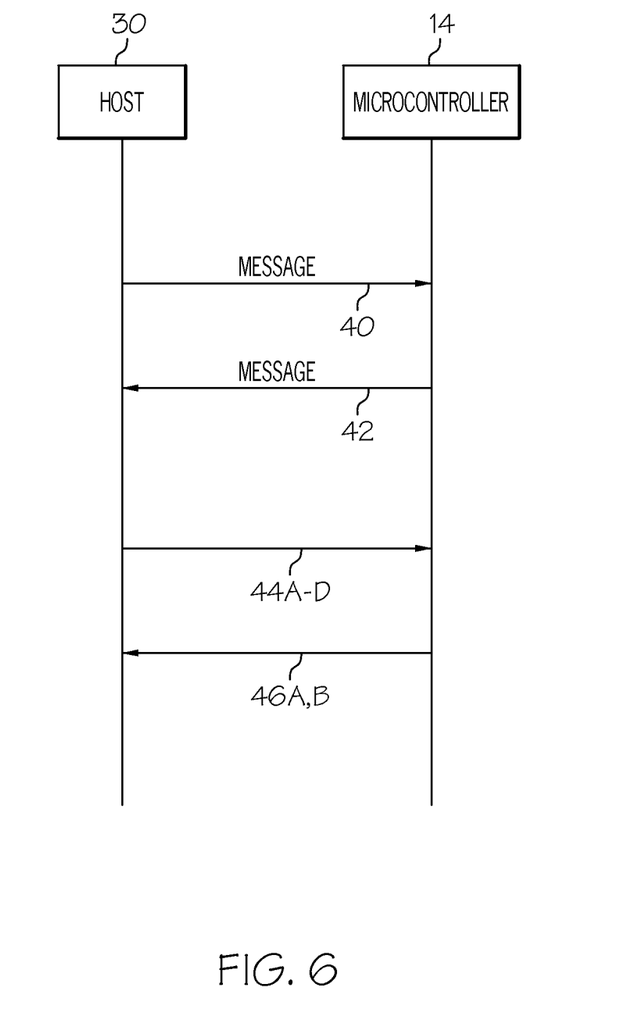
FIG. 6 depicts the communication between the host and the embeddable module according to one or more embodiments shown and described herein.

Referring now to FIG. 6, one embodiment of the communication scheme between the host and the microcontroller is depicted. The microcontroller may normally wait for a message from the host 40 before initiating a message. Upon reception of a message from the host 40, the microcontroller (through the operation of the module software) may respond with a message to the host 42. The messages 40, 42 sent between the host and module may be serial in nature and may be implemented by a UART or IrDA. As such, the serial messages may include a start of transmission byte, one or more data bytes, a cycle redundancy check (CRC) byte, and an end of transmission byte. The serial message may comprise other protocols, as may be known in the art.

Furthermore, the serial communication scheme shown in FIG. 6 may be enhanced by additional discrete signals 44, 46. For example, the host may send the module a "Module Reset" signal 44A, a "Module Interrupt" signal 44B, a "Button Right" signal 44C, and a "Meter Configuration" signal 44D. The Module Reset signal 44A may reset the microcontroller without resetting the ASIC. The Module Interrupt signal 44B may interrupt the microcontroller in order for the host to get the attention of the microcontroller. This signal may also turn off the module unless a bG test is in progress. The "Button Right" signal 44C may interrupt the microcontroller in order for the host to get the attention of the microcontroller without turning off the module. The Meter Configuration signal 44D may provide a voltage level to the microcontroller to determine its behavior during start up with a measurement strip having a "Safe Mode" characteristic. Other similar signals may be used as in known in the art.

As another example, the module may send to the host an "Event Interrupt" signal 46A and a "Module Ready" signal 46B. The Event Interrupt signal 46A may indicate to the host that an event has occurred on the module, such as a measurement strip was inserted in the measurement strip port. The Module Ready signal 46B may indicate to the host that the module is ready to receive a serial message from the host. Other similar signals may be used as is known in the art.

Figure 7:
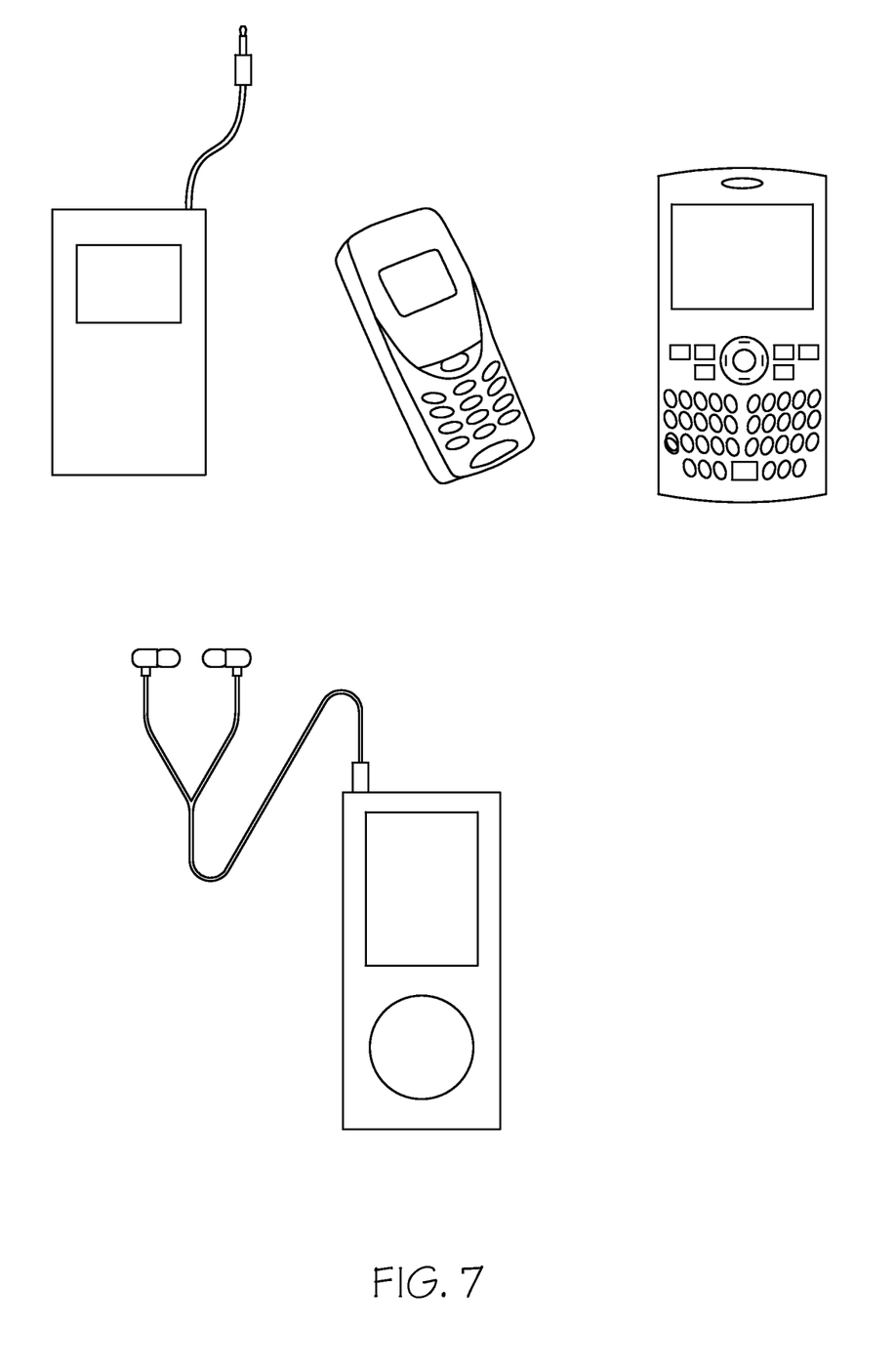
FIG. 7 depicts various types of hosts according to one or more embodiments shown and described herein.

Referring to FIG. 7, various embodiments of the host are shown. It is contemplated that the embeddable module may be installed in a plurality of external hosts, including but not limited to insulin pumps, cellular phones, smart phones, music players, and similar devices. These devices may be portable and may operate from a battery. The embeddable module, when installed, may also operate from the same battery as the host. The embeddable module may assume a number of shapes and geometries in order to be installed in the host. For example, as shown in the embodiment in FIG. 5, the module may assume a substantially rectangular shape, approximately 25 mm by 35 mm. In other embodiments, the module may assume an irregular shape in order to be installed in an external host without interfering with obstructions, such as electrical or mechanical components in the host. Furthermore, the embeddable module may comprise two or more smaller modules coupled together. For example, the module may comprise a primary circuit board with one or more secondary circuit boards installed on the primary circuit board.

The embeddable module may be designed to be permanently embedded in the external host. Although the design of the module may make it relatively easy to install the module in the host, it is contemplated that the module normally will not be removed once installed. For example, the embeddable module may be installed in a cellular phone which is subsequently sold to consumers. The consumers may observe that the cellular phone has a measurement strip port and possibly a code key port. However, there may be no other indications to the consumers that an embeddable bG module has been installed in the cellular phone. Furthermore, the consumers may not be able to remove the embeddable module since this may require disassembly of the cellular phone. Thus, in some embodiments, the embeddable module may be permanently installed in the external host.

Still another embodiment of the embeddable module for measuring blood glucose levels may include a Universal Serial Bus device. The Universal Serial Bus (USB) is a method of exchanging data developed and supported by USB Implementers Forum, Inc. In this embodiment, the module may be embedded in a portable USB device which may be carried around by the user. The USB device may contain a measurement strip port and a code key port and may be operable to be installed in a mating USB port in an electronic host device, such as a personal computer (i.e., a desktop or laptop). When the user wishes to take a bG measurement, he may simply insert the USB device into a mating USB port of the electronic host device. The host device may supply electrical power to the USB device and may also contain the software necessary to communicate to the USB device. For this embodiment, the host interface may be a USB interface. The remaining components of the embeddable module may function as previously described.

It should now be understood that the modules described herein may be embedded in a host so as to provide the host with the capability of measuring blood glucose levels. The module may be operable to be embedded in the host and to communicate to the host through the host interface. The module is operable to perform a blood glucose measurement and to communicate the measurement result to the host via the host interface.

While particular embodiments and aspects of the present invention have been illustrated and described herein, various other changes and modifications may be made without departing from the spirit and scope of the invention. Moreover, although various inventive aspects have been described herein, such aspects need not be utilized in combination. It is therefore intended that the appended claims cover all such changes and modifications that are within the scope of this invention.

What is claimed is:

1. A blood glucose measurement module embeddable in an external host for measuring a blood glucose level of a blood sample provided on a disposable measurement strip, the module consisting of:
   a host interface;
   a microcontroller;
   an application-specific integrated circuit (ASIC);
   a temperature measuring element;
   a measurement strip port,
   an external code key separate from the measurement strip and configured to contain calibration information related to the measurement strip,
   a code key port configured to receive the external code key wherein the code key port resides completely within a housing of the host; and
   a non-volatile memory;
   wherein:
   the host interface is operable to permit electrical communication between the host and the microcontroller such that the module is operable to transmit a result of a blood glucose level measurement to the host and the module is operable to send to the host an event interrupt signal to indicate to the host that an event has occurred on the module and to send to the host a module ready signal to indicate to the host that the module is ready to receive a message from the host, wherein the event comprises detecting insertion of the measurement strip into the measurement strip port;
   the microcontroller is in electrical communication with the ASIC wherein the microcontroller and the ASIC are operable to measure the blood glucose level of the blood sample,
   the measurement strip port is operable to receive the disposable measurement strip having the blood sample,
   the ASIC is in electrical communication with the measurement strip port such that the ASIC is operable to receive signals from the measurement strip port related to the blood glucose level of the blood sample provided on the measurement strip,
   the temperature measuring element is in electrical communication with the microcontroller and is operable to measure the temperature of the module and transmit signals to the microcontroller related to the temperature of the module; and
   wherein the non-volatile memory is operable to store data relating to the operation of the module or calibration data for the measurement strip, wherein the non-volatile memory is in electrical communication with the microcontroller such that the microcontroller is operable to read data from and write data to the memory.

2. The blood glucose measurement module of claim 1 wherein:
   the code key is operable to be removably connected to the module; and
   the microcontroller is in electrical communication with the code key such that the microcontroller is operable to read the calibration data stored on the code key when the code key is connected to the module.

3. The blood glucose measurement module of claim 1 wherein the module is operable to request calibration data for the measurement strip from the host.

4. The blood glucose measurement module of claim 1 wherein the host is in electrical communication with the code key having calibration data for the measurement strip and is operable to communicate the calibration data to the microcontroller via the host interface.

5. The blood glucose measurement module of claim 1 wherein the microcontroller comprises a non-volatile memory operable to store data relating to the operation of the module or calibration data for the measurement strip.

6. The blood glucose measurement module of claim 1 wherein the host interface is a wired serial interface, a wired parallel interface, or an infrared serial interface.

7. The blood glucose measurement module of claim 1 wherein the host is an insulin pump, a cellular phone, a smart phone, a PDA, or a music player.

8. The blood glucose measurement module of claim 1 wherein the temperature measuring element is a semiconductor sensor, a resistance thermal device (RTD), or a thermocouple.

* * * * *

UNITED STATES PATENT AND TRADEMARK OFFICE
CERTIFICATE OF CORRECTION

| | | |
|---|---|---|
| PATENT NO. | : 8,636,661 B2 | |
| APPLICATION NO. | : 12/477982 | |
| DATED | : January 28, 2014 | |
| INVENTOR(S) | : Carol Batman et al. | |

It is certified that error appears in the above-identified patent and that said Letters Patent is hereby corrected as shown below:

In the Specification:

Col. 4, Line 45, "As previously, discussed herein," should read
--As previously discussed herein,--;

Col. 4, Line 65, "in order function" should read --in order to function--;

Col. 6, Line 45, "may in" should read --may be in--;

Col. 7, Line 36, "direction communication" should read --direct communication--;

Col. 8, Line 16, "such a UART" should read --such as an UART--; and

Col. 10, Line 54, "used as in known in the art." should read --used as is known in the art.--.

Signed and Sealed this
First Day of July, 2014

Michelle K. Lee
*Deputy Director of the United States Patent and Trademark Office*